United States Patent [19]
Dumoulin et al.

[11] Patent Number: 5,807,253
[45] Date of Patent: Sep. 15, 1998

[54] PATIENT ELECTRICAL ISOLATION SYSTEM

[75] Inventors: Charles Lucian Dumoulin, Ballston Lake; Kenneth William Rohling, Burnt Hills; Ronald Dean Watkins, Niskayuna; Randy Otto John Giaquinto, Burnt Hills, all of N.Y.

[73] Assignee: General Electrical Company, Schenectady, N.Y.

[21] Appl. No.: 944,631

[22] Filed: Oct. 6, 1997

[51] Int. Cl.[6] .................................................. A61B 1/00
[52] U.S. Cl. ............................................ 600/410; 128/908
[58] Field of Search ..................................... 600/407, 410, 600/305, 134; 128/908, 897; 607/63

[56] References Cited

U.S. PATENT DOCUMENTS

| | | | |
|---|---|---|---|
| 3,690,313 | 9/1972 | Weppner et al. | 600/300 |
| 4,461,302 | 7/1984 | Phillips et al. | 600/300 |
| 4,742,831 | 5/1988 | Silvian | 600/523 |
| 4,853,772 | 8/1989 | Kikuchi | 358/98 |
| 4,969,885 | 11/1990 | Farin | 606/38 |
| 5,125,410 | 6/1992 | Misono et al. | 600/462 |
| 5,139,021 | 8/1992 | Sekii et al. | 600/300 |
| 5,246,439 | 9/1993 | Hebborn et al. | 606/35 |
| 5,284,151 | 2/1994 | Onoda | 600/523 |
| 5,307,817 | 5/1994 | Guggenbuhl et al. | 600/509 |
| 5,418,686 | 5/1995 | Dieken et al. | 128/908 |
| 5,480,399 | 1/1996 | Hebborn | 606/35 |
| 5,671,738 | 9/1997 | Thornberg | 600/407 |

*Primary Examiner*—Brian Casler
*Attorney, Agent, or Firm*—Lawrence P. Zale; Marvin Snyder

[57] ABSTRACT

A patient isolation device is used as a safety device to provide electrical insulation between medical electronic equipment and portions of the equipment which come in contact with the patient. In one implementation of the patient isolation device, an RF coil is incorporated in a catheter connected to medical electronic equipment which tracks the position of the catheter. Typically, there is also medical imaging electronics to provide internal images of the subject along with an indication of the location of the catheter. Typically, the signal from the RF coil is provided to a preamplifier to amplify the signal. The isolation device is placed between the RF coil and the preamplifier such that MR response signals may pass through to the preamplifiers but in the event of a short or electrical malfunction the line voltage will not pass backward into the RF coil causing damage to the patient.

5 Claims, 2 Drawing Sheets

PATIENT ELECTRICAL ISOLATION SYSTEM

BACKGROUND OF THE INVENTION

1. Field of the Invention

This invention relates to a medical safety device, and more particularly, a system for electrically isolating a patient from medical equipment.

2. Discussion of Prior Art

Many conventional medical procedures involve imaging of internal organs of a subject during a medical procedure in order to guide a physician around structures such has vessels, and nerves.

There are also invasive medical procedures in which a device, such as a catheter has a radiofrequency (RF) coil incorporated in it for the purpose of acquiring magnetic resonance (MR) signals to be used either for locating the catheter and/or providing an MR image.

Patients undergoing medical imaging must be protected from failures of the medical imaging apparatus and other medical equipment connected to the patient. Due to the nature of magnetic resonance (MR) imaging, special requirements exist. In non-interventional (no devices are inserted into the subject) MR imaging, isolation of the patient from the MR imaging system is accomplished by incorporating insulating materials in the construction of surfaces which the patient is likely to touch (e.g. surface coils, patient bed, etc.).

For interventional procedures, the issue of patient isolation is more complicated since interventional devices are in contact with the subject. This can be especially critical if the invasive device is in contact with electrically-sensitive tissue (e.g. cardiac muscle; brain tissue, etc.)

Construction of an isolation circuit that works under MR conditions is not straightforward. The following requirements need to be met by an isolation device which is intended to protect a patient undergoing an interventional procedure in which a device such as an MR receive coil is simultaneously placed within a subject and connected to an external medical device.

1. A high degree of electrical isolation must be provided. This isolation must be sufficient to protect the subject from current arising from ground loops and catastrophic failure of medical equipment.
2. The isolation circuit must be able to pass very low-level radiofrequency signals such as those induced by an MR coil without introducing a substantial amount of noise.
3. The isolation circuit must be able to function in the presence of a strong magnetic field.
4. The isolation circuit must be tolerant of failures.
5. The isolation circuit must be small enough to fit into a suitably sized housing.
6. And, the isolation circuit must be stable and resist changes in performance.

Many conventional isolation circuits employ a ferrite core. When these circuits are immersed in a strong magnetic field of an MR imager, the ferrite core will saturate resulting in a loss of coupling between the secondary and primary windings of the transformer.

Also, an MR imager produces rapidly changing magnetic fields during the production of field gradients used in imaging. The changing magnetic fields can induce currents in an inappropriately designed isolation circuit.

Conventional optical isolation means are not well suited for use with invasive devices which require power from the medical equipment, since additional isolated means must be supplied to provide power to the detector device. Furthermore, use of optical isolation in a circuit intended to propagate low level signals, such as those acquired during MR Imaging procedures would degrade the signal-to-noise ratio of the detected signals.

Capacitative coupling by itself is also not well suited due to the large physical device size that would be required to provide a double-barrier isolation with an acceptable level of leakage current.

Currently there is a need for a device which can pass a limited amount of electrical power from medical equipment to devices in or near a subject, while passing a magnetic resonance (MR) or similar signal from the subject back to the medical equipment.

BRIEF DESCRIPTION OF THE DRAWINGS

The features of the invention believed to be novel are set forth with particularity in the appended claims. The invention itself, however, both as to organization and method of operation, together with further objects and advantages thereof, may be best understood by reference to the following description taken in conjunction with the accompanying drawing in which:

SUMMARY OF THE INVENTION

Figure 1:
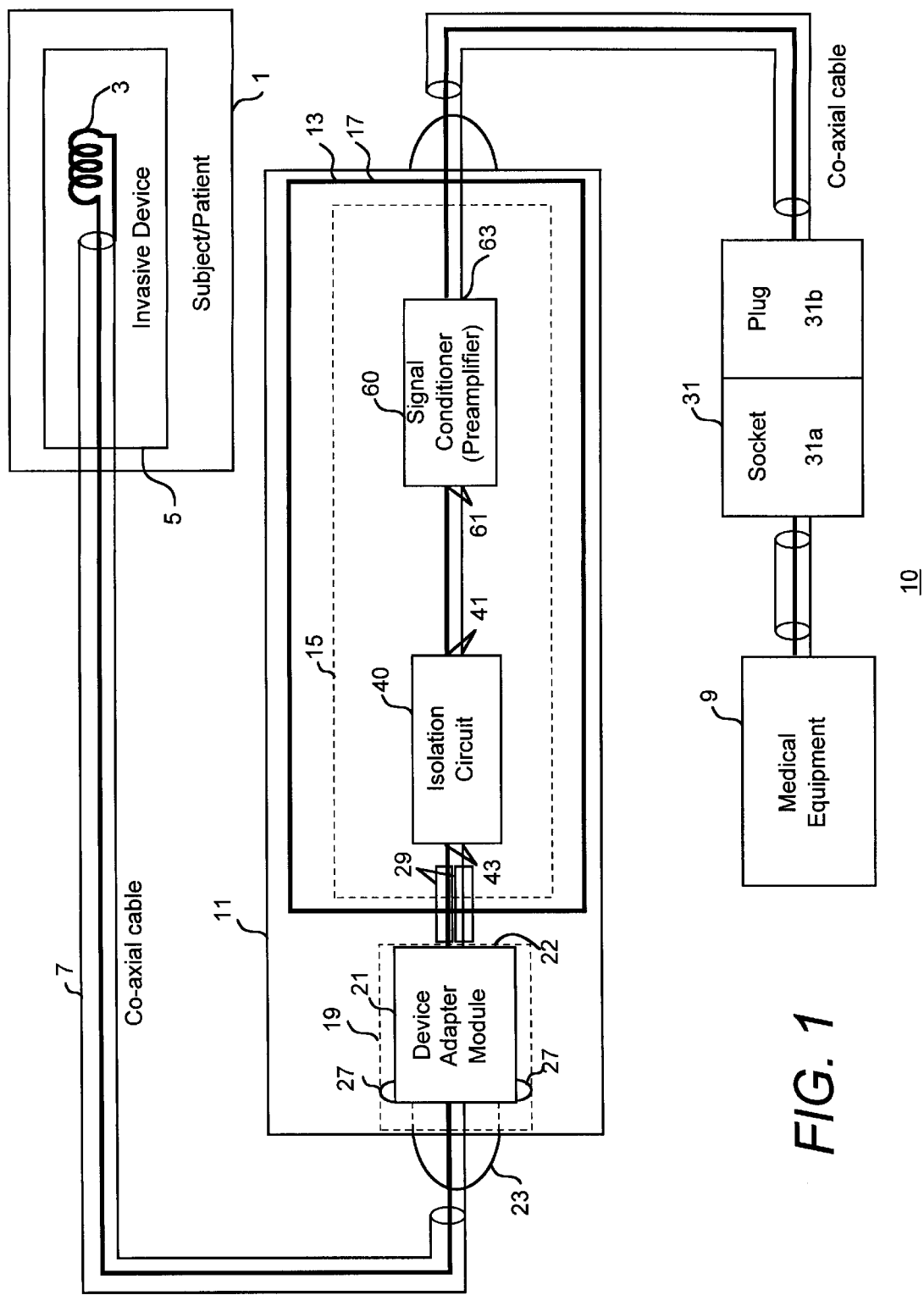
FIG. 1 is a simplified block diagram of one embodiment of the present invention in use connected between an invasive device and medical equipment.

An electrical isolation system is intended for use in a sterile environment. It functions to restricting power passing from medical equipment backward to medical apparatus, such as a catheter, in contact with a subject.

A hermetically sealed housing has a main compartment with an adapter compartment and a separator wall between the main and adapter compartments;

A device adapter module fits snugly within the adapter compartment, employing a substantially waterproof plug seal.

A medical apparatus is connected to an instrument plug which is connected to the device adapter module.

An isolation circuit is sealed within the main housing coupled to the device adapter module through the separator wall.

For use in a magnetic resonance (MR) imaging environment, the isolation transformer employs an air core transformer for inductively coupling a set of input leads to a set of output leads. Since an iron core is not used, interference with a magnetic field of an MR imaging device is minimized. This reduces the distortion and attenuation of an acquired MR signal.

The isolation transformer employs coils and capacitors tuned to pass a narrow signal band corresponding to the frequency band of a signal desired to be received from the medical apparatus.

If the medical apparatus is an MR receive or tracking coil, the band passed corresponds to an MR response signal acquired in the specific magnetic field used in the MR imaging.

The isolation transformer blocks substantially all other unwanted power transmission from the medical equipment to the medical apparatus.

A preamplifier is also sealed within the main compartment coupled to the isolation transformer. The main compartment is intended to be opened only by authorized service personnel. However, the elements in the adapter compartment are intended to be changed by medical personnel, if desired.

A quick disconnect plug has a fixed side and a disconnect side designed to fit together to passing a signal between them. These sides are easily pulled apart without the need of a tool, for physical disconnection of the medical equipment from the patient and medical apparatus, allowing easy removal of the subject which may be especially valuable during an emergency. Disconnection also stops passage of a signal from medical apparatus to the medical equipment.

OBJECTS OF THE INVENTION

It is an object of the present invention to provide a device which protects a subject from electrical shock from an invasive device thereby preventing cardiac problems.

It is another object of the present invention to provide a device which protects a subject from electrical shock from medical equipment connected to an invasive device in or near the subject.

It is another object of the present invention to pass weak imaging signals from a subject preserving high signal-to-noise ratios, while limiting the power passed back to the subject.

DETAILED DESCRIPTION OF THE INVENTION

Theory

In designing an isolation circuit, it was determined that a system which would pass a narrow band signal tuned to the correct frequency will be more efficient than a broad band circuit.

It was also determined that a ferrite core transformer could not be used.

The system should have quick disconnect capabilities in the event of an emergency and the subject had to be disconnected from the medical equipment and moved.

Since it is used in medical procedures, the isolation circuit must be hermetically sealed and sterilizable.

Overview

A simplified block diagram of the patient isolation system 10 for tracking a single coil according to the present invention is shown in FIG. 1. An RF coil 3 is incorporated into invasive device 5 located in or near subject 1. The isolation system 10 has several major components:

a) a hermetically sealed housing 11;
b) a device adapter module 21;
c) an isolation circuit 40;
d) a signal conditioning circuit 60; and
f) a quick disconnect assembly 31.

Housing

In FIG. 1 a patient isolation system according to the present invention is shown in a semi-schematic plan view. A housing 11 has a groove 13 which encompasses the top and encloses a main compartment 15. A housing seal 17 fits within groove 13 and against a top (not shown) to hermetically seal main compartment 15. No user serviceable parts are contained within the main compartment.

An adapter compartment 19 receives a device adapter module 21. Device adapter module 21 has an instrument plug 23 and optionally may contain a tuning/matching circuit (not shown). A plug seal 27 seals adapter compartment 19.

Electrical connectors 29 have a portion which is embedded in housing 11 and attached to isolation circuit 40, and a portion which connects to device adapter module 21 which allows secure electrical contact between them.

Device Adapter Module

Instrument plug 23 is of the type to mate with given types of electrical connectors. For example, it may be a BNC type, SMA, RJ-11, etc. Since this is intended to be used in a sterile environment, it is important that it may be sterilized and hermetically sealed such that it may maintain its sterility. Device adapter module 21 is designed, be changed by the user to permit any number of different devices to be connected to the MR imaging system. If desired, a tuning/matching circuit can be incorporated into the device adapter module to maximize the signal-to-noise ratio of the signals being sent from invasive device 5 through isolation system 10. Therefore, device adapter module 21 is designed to be quickly pulled out and removed in order to put in another device adapter module 21 having a different instrument plug which corresponds to the new cables or device to be connected. This may be done during a medical procedure without breaking sterility.

Quick Disconnect Assembly

Patient isolation system 10 is intended to connect instrument plug 23 with instruments intended to be used in or near the subject. The other end of patient isolation system 10 has a quick disconnect assembly 31 which connects to the remaining medical imaging, or other medical equipment 9. The purpose of patient isolation system 10 is to pass signals from instrument plug 23 to quick disconnect assembly 31 without causing power to pass in the reverse direction from the medical equipment.

Quick disconnect assembly 31 incorporates a plug 31b and a socket 31a to provide a quick means of disconnecting the entire patient isolation system from the medical electronics in the case of an emergency. This allows subject 1 to be quickly removed from the medical imaging equipment and the emergency procedures be performed on subject 1.

Isolation Circuit

Inside main compartment 15, an isolation circuit 40 provides the electrical isolation and is designed to be used, in or near, a high magnetic field which is commonly used in MR imaging. A signal conditioning circuit 60 is connected to isolation circuit 40 and amplifies the signal from isolation circuit 40 and provides the amplified signal to quick disconnect plug 31b and ultimately to the medical equipment.

A medical apparatus 5, such as an invasive device, is in contact with living subject 1 for various medical purposes. This may be invasive and inserted into subject 1, or attached to subject 1.

In one embodiment, an RF coil 3 is attached to invasive devices, such as a catheter, and is used for tracking the location of invasive device 5 within subject 1. Alternatively, RF coil 3 could be used to perform internal imaging. The signals from RF coil 3 are then provided to instrument plug 23 via a cable 7. Patient isolation system 10 then provides the signal through quick disconnect assembly 31 to medical equipment 9.

Air Core Transformer

Figure 2:
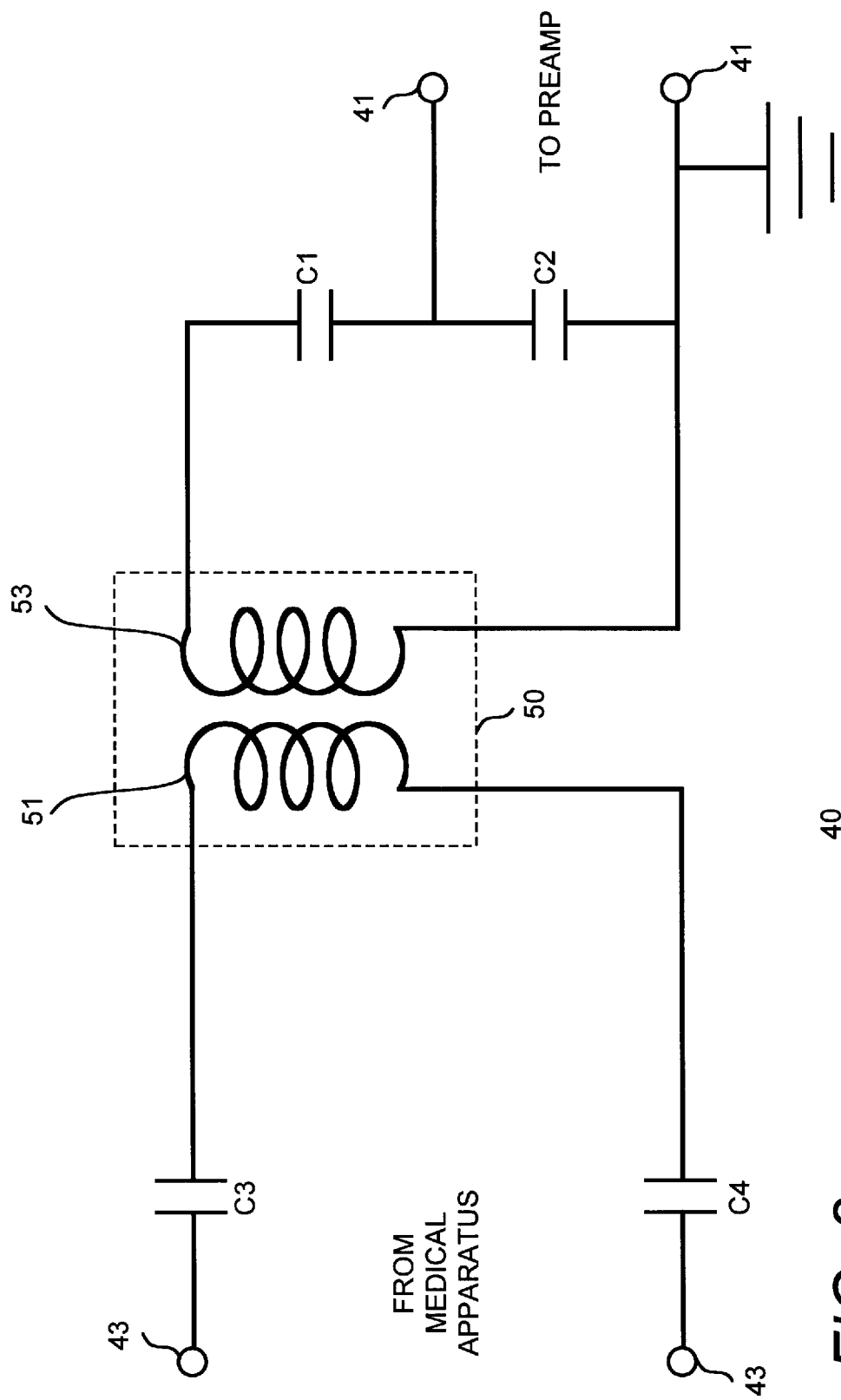
FIG. 2 is a schematic drawing of the isolation circuit of FIG. 1 according to the present invention.

In the present invention, electrical isolation between the patient and the imaging system is achieved with an isolation circuit 40 having an air core transformer 50 in combination with capacitors C1, C2, C3, C4 as shown in the schematic drawing of FIG. 2. The purpose of isolation circuit 40 is to provide an electrical barrier between a set of leads 41 in communication with medical equipment 9, and a set of leads 43 in communication with apparati in contact with subject 1. Isolation circuit 40 is designed to protect subject 1 even if full line voltage appears at a set of input leads 61 attached to signal conditioner circuit 60, and one of the blocking capacitors (C3 or C4) shorts, thereby substantially stopping current flow through leads 43.

In the presently preferred embodiment, air core transformer 50 is constructed by winding two interleaved coils 51, 53 on a hollow cylindrical fiberglass tube. Both coils 51, 53 should have an equal number of turns if the input voltage is to equal the output voltage. Alternatively, the number of turns could be adjusted to produce voltage step-up, or step-down, if desired.

Each coil 51, 53 is constructed with an insulated wire. The insulation is chosen to be able to withstand high voltages. The insulation on each wire provides a barrier such that two simultaneous failures are required if the isolation is to be compromised.

Since isolation transformer 50 is tuned to pass signals of a given frequency range, and the frequency range of a received MR response signal changes with the main magnetic field used in magnetic resonance imaging, the capacitance values must change for different magnetic field strengths. In the present embodiment these capacitors have the following values:

|  | Field Strength | | |
| --- | --- | --- | --- |
|  | 0.2 Tesla | 0.5 Tesla | 1.5 Tesla |
| C1 | 528 pF | 140 pF | 0 pf |
| C2 | 1360 pF | 190 pF | 25 pf |
| C3, C4 | 0.1 $\mu$F | 0.01 $\mu$F | 0.01 $\mu$F |

Transformer 50, constructed on a 0.625 in. outer diameter fiberglass cylinder, 1.25 in. long, having 2 coils with 11 turns each of Teflon wire, was tested to have a leakage current less than 2 $\mu$A at 50 Hz when 120 volts AC are applied to the secondary. The isolation transformer has been Hi-Pot tested to 4000 volts with good results.

Multiple Channel Embodiment

In an alternative embodiment of the present invention a plurality of medical apparati are in contact with subject 1. The circuit of FIG. 1 is duplicated several times, once for each of the medical apparatus. These parallel circuits allow separate isolation systems for each device in contact with the patient. Failure of one will not affect the isolation of the other apparati, leaving the other channels operational.

Variations Of The Invention

Although the invention is described above as an MR receiver coil, the isolation techniques used here are suitable for use with any electrical device which is placed on or near subject 1 during a medical procedure. These devices include pressure sensors, ultrasonic transducers, tissue abalaters, etc., and the present invention may function equally well with each of these.

While several presently preferred embodiments of the novel invention have been described in detail herein, many modifications and variations will now become apparent to those skilled in the art. It is, therefore, to be understood that the appended claims are intended to cover all such modifications and variations as fall within the true spirit of the invention.

What we claim is:

1. An electrical isolation system for use in a sterile environment, functioning to restricting power from passing from medical equipment to an invasive device in contact with a subject comprising:

a) a hermetically sealed housing having a main compartment, an adapter compartment and a separator wall between the main and adapter compartments;

b) an isolation circuit within the housing, having input leads and output leads, with the input leads adapted to be coupled to said invasive device, the isolation circuit tuned to pass a signal band to its output leads being substantially a frequency band of signals desired to be received from the medical equipment while blocking substantially all other unwanted power transmission;

c) a signal conditioning circuit within the main compartment, having input and output leads with its input leads communicating with the output leads of the isolation circuit;

d) a quick disconnect assembly having a socket and a plug designed to fit together passing a signal between the plug communicating with signal conditioning circuit and the socket communicating with said medical equipment, designed to be manually disconnected, facilitating removal of the subject from the medical equipment.

2. The electrical isolation system of claim 1 wherein the isolation circuit comprises:

an air core transformer for inductively coupling the input leads to the output leads which minimizes interference with a magnetic field of a magnetic resonance (MR) imaging device thereby electrically isolating a subject without appreciably distorting an acquired MR signal.

3. The electrical isolation system of claim 1 further comprising:

a device adapter module fitting within the adapter compartment, having an instrument plug having outside electrical connections for connecting a cable in correspondence with medical apparatus, fitting snugly in the adapter compartment employing a substantially waterproof plug seal, also having internal electrical connections coupled to said isolation circuit.

4. The electrical isolation system of claim 1 wherein signal conditioning circuit comprises:

a preamplifier which receives an input signal and amplifies the the signal.

5. An electrical isolation system for use in a sterile environment, functioning to restricting power from passing from medical equipment to a plurality of medical apparati in contact with a subject comprising:

a plurality of electrical isolation circuits, each isolation circuit comprising:

a) a hermetically sealed housing having a main compartment, a plurality of adapter compartments and a separator wall between the main compartment and adapter compartments;

b) a plurality of isolation circuits within the main housing, having input and output leads, with the input leads, adapted to be coupled to said medical apparati, the isolation circuits tuned to pass a signal band being substantially a frequency band of signals desired to be received from the medical apparati, while blocking substantially all other unwanted power transmission;

c) a plurality of signal conditioning circuits within the main compartment, having input leads and output leads, with its input leads communicating with the output leads of the isolation circuit;

d) a quick disconnect assembly having a socket and a plug designed to fit together passing a signal between the plug communicating with signal conditioning circuit and the socket communicating with said medical equipment, designed to be manually disconnected, facilitating removal of the subject from the medical equipment.

\* \* \* \* \*